United States Patent
Rocha-Sanchez (12) 
(10) Patent No.: US 9,925,185 B1
(45) Date of Patent: Mar. 27, 2018

(54) TREATMENT AND PREVENTION METHODS FOR MAMMALIAN NEUROSENSORY HAIR CELLS LOSS

(71) Applicant: Creighton University, Omaha, NE (US)

(72) Inventor: Sonia M. Rocha-Sanchez, Omaha, NE (US)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 14/958,465

(22) Filed: Dec. 3, 2015

Related U.S. Application Data (60) Provisional application No. 62/086,852, filed on Dec. 3, 2014.

(51) Int. Cl.
*A61K 31/498* (2006.01)
*A61K 33/24* (2006.01)

(52) U.S. Cl.
CPC ............ *A61K 31/498* (2013.01); *A61K 33/24* (2013.01)

(58) Field of Classification Search
None
See application file for complete search history.

(56) References Cited

FOREIGN PATENT DOCUMENTS

WO    WO 2008/013866 A2 *  1/2008

OTHER PUBLICATIONS

Duan et al. "Low Dose, Long-Term Caroverine Administration Attenuates Impulse Noise-Induced Hearing Loss in the Rat". Acta Oto-Laryngologica. 2006; 126(11):1140-1147.*
Shin et al. "A Novel Synthetic Compound, 3-Amino-3-(4-Fluoro-Phenyl)-1H-Quinoline-2,4-Dione, Inhibits Cisplatin-Induced Hearing Loss by the Suppression of Reactive Oxygen Species: In Vitro and In Vivo Study". Neuroscience. 2013; 232:1-12.*
STN Registry No. 23465-76-1. "Caroverine". [Retrieved from STN Registry Mar. 6, 2017]. One page.*

* cited by examiner

*Primary Examiner* — Lesie A. Royds Draper
(74) *Attorney, Agent, or Firm* — Advent, LLP (57) ABSTRACT

The present disclosure relates to methods of treating acquired sensorineural hearing loss and/or ototoxicity in mammals by administering quinoxaline or a pharmaceutically acceptable derivative thereof. In implementations, quinoxaline and its derivatives can decrease cochlear hair cell damage and/or stimulate cochlear hair cell proliferation. In some implementations, quinoxaline can be administered as a pre-treatment prior to, or in conjunction with, exposure to ototoxic pharmaceutical agent(s) and/or acoustic trauma to prevent or decrease cochlear hair cell cytotoxicity and/or stimulate cochlear hair cell proliferation. In other implementations, quinoxaline can be administered as a treatment following exposure to ototoxic pharmaceutical agent(s) and/or acoustic trauma to stimulate cochlear hair cell proliferation.

20 Claims, 6 Drawing Sheets

TREATMENT AND PREVENTION METHODS FOR MAMMALIAN NEUROSENSORY HAIR CELLS LOSS

BACKGROUND

Acquired sensorineural hearing loss is hearing loss that occurs after birth. Common causes can include, but are not limited to aging, exposure to harmful noise, disease or infection, head or acoustic trauma, tumors, and exposure to ototoxic or ototraumatic pharmaceutical agents. Ototoxicity is the property of being toxic to the ear. Ototoxicity can result as a side effect of drug therapy. Ototoxicity can result in sensorineural hearing loss, dysequilibrium, or both. The effects of ototoxicity can be reversible and temporary, or irreversible and permanent.

SUMMARY

The present disclosure relates to methods of treating acquired sensorineural hearing loss and/or ototoxicity in mammals by administering quinoxaline or a pharmaceutically acceptable derivative thereof. In implementations, quinoxaline and its derivatives can decrease cochlear hair cell damage and/or stimulate cochlear hair cell proliferation.

In some embodiments, quinoxaline can be administered as a pre-treatment and/or treatment for acquired sensorineural hearing loss linked to damage of cochlear hair cells. For example, quinoxaline can be administered to humans or other mammals to prevent and/or treat ototoxicity and hearing loss resulting from ototoxic pharmaceutical agents. In some implementations, quinoxaline can be administered in conjunction with an ototoxic pharmaceutical agent. In other implementations, humans or other mammals can be pre-treated with quinoxaline prior to exposure to the ototoxic pharmaceutical agents. In some implementations, quinoxaline can be administered alone to stimulate ear cell proliferation.

In other embodiments, quinoxaline can be administered as a pre-treatment and/or treatment to humans or other mammals to prevent and/or treat hearing loss caused by acoustic trauma (e.g., exposure to harmful noises). In some implementations, quinoxaline can be administered prior to anticipated exposure to a potentially traumatic stimuli (e.g., harmful noise of 85 dB or greater). In other embodiments, quinoxaline can be administered following exposure to a potentially traumatic stimuli (e.g., harmful noise of 85 dB or greater) to stimulate cochlear hair cell proliferation.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

DETAILED DESCRIPTION

Overview

Acquired sensorineural hearing loss is hearing loss that occurs after birth. Common causes can include, but are not limited to aging, exposure to harmful noise, disease or infection, head or acoustic trauma, tumors, and exposure to ototoxic or ototraumatic pharmaceutical agents.

Acquired sensorineural hearing loss is linked to trauma and degeneration of cochlear hair cells and their associated spiral ganglion neurons (SGNs). Mammalian inner ear hair cells proliferate during embryogenesis, exit the cell cycle, differentiate, and become functionally mature. Sensory hair cells in the mammalian cochlea convert mechanical stimuli into electrical impulses, which are essential for hearing and balance. Postmitotic hair cells do not regenerate and their death leads to irreversible hearing and balance impairment.

Noise-induced hearing loss, or hearing loss resulting from acoustic trauma, is a common cause of acquired sensorineural hearing loss. Acoustic trauma can result from high-intensity and/or prolonged exposure to noise. Approximately 15 percent of Americans between the ages of 20 and 69 suffer from noise-induced hearing loss. Noise-induced hearing loss can result from continuous exposure to moderate noises (e.g., 85 decibels or greater) over a period of time, or one-time exposure to loud noises (e.g. 140 decibels or greater).

Exposure to ototraumatic or ototoxic pharmaceutical agents is another common cause of acquired sensorineural hearing loss. Ototraumatic or ototoxic pharmaceutical agents are those with the potential to cause toxic reactions to the neurosensory epithelia of the inner ear (e.g., the cochlea and the five vestibular end-organs), resulting in hair cell death. Currently, there are more than 200 known ototoxic pharmaceutical agents available on the market ranging from prescription to over-the-counter medications. Some ototoxic pharmaceutical agents can include antibiotics, platinum-based antineoplastic agents, salicylates, quinine, and loop-diuretic drugs, among others. Ototoxic side effects normally occur within days or weeks after systemic application and are often bilateral in presentation. The irreversible nature of hearing loss or balance impairment may have serious communication, educational, behavioral, psychological, and social consequences.

While the mechanism underlying ototoxicity may be complex, there are a number of suspects believed to be involved in the damaged hair cells' death cascade. Of fundamental interest is the involvement of electron transfer (ET), the activity of reactive oxygen species (ROS), oxidative stress (OS), cell signaling, and/or receptors. ET, ROS, and OS have been increasingly implicated in the mode of action of drugs (e.g., anticancer drugs, antibiotics, and abused drugs) and toxins (e.g., carcinogens, reproductive toxins, cardiovascular toxins, etc), including ototoxins and noise-induced hearing loss. ET activity is a major source of ROS. Redox cycling with oxygen, as well as disruption of the mitochondrial ET chain after exposure to ototoxins, give rise to ROS, hence triggering OS. As previously demonstrated in different biological systems, including the inner ear, an increase in intracellular ROS ultimately activates caspase 3, which plays a central role in causing apoptotic cell death. To date, there is no effective method to either prevent or reverse the toxic cellular effects associated with elevated ROS production. Likewise, there are no therapies available to reverse ototoxic damage.

Figure 1:
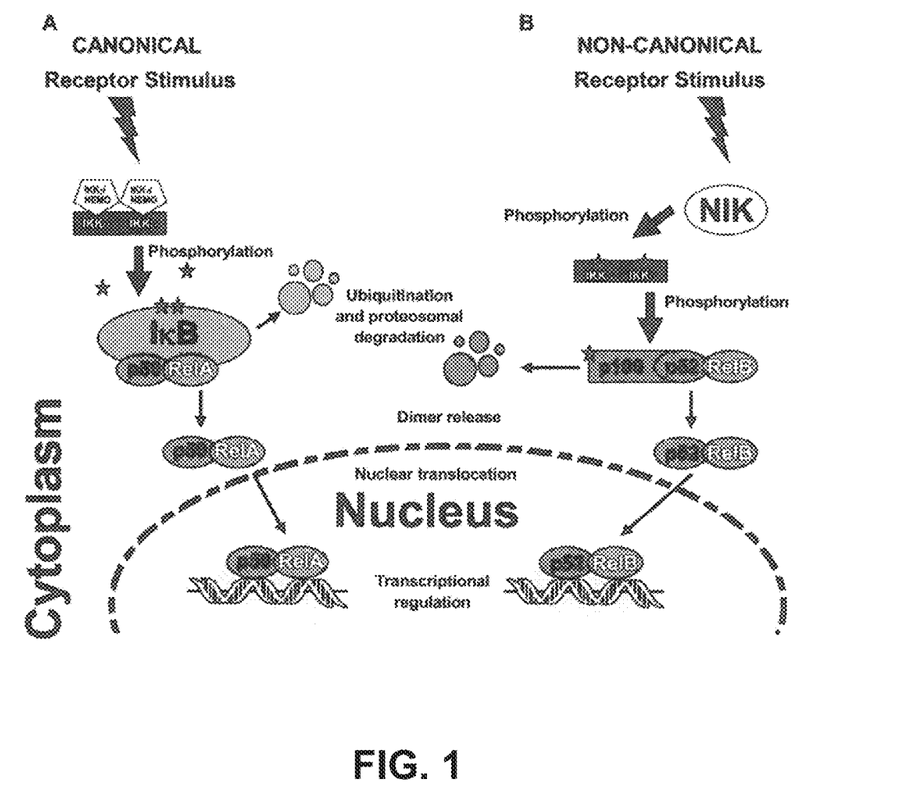
FIG. 1 is a graphical illustration depicting pathways leading to activation of the NF-κB signaling cascade.

ROS have various inhibitory or stimulatory roles in NF-κB Signaling. The transcription factor NF-κB is normally held in the cytoplasm via the inhibitor of NF-κB (1κB). After phosphorylation by IκB kinase (IKKκ), IκB is degraded, leading to NF-κB activation. The NF-κB signaling pathway plays a central role in cell proliferation, differentiation, and apoptosis in almost all cells in the body, as illustrated in FIG. 1. NF-κB proteins are a family of structurally and evolutionarily conserved transcription factors expressed in all cell types. This family is composed of five subunits (p65/ReIA, c-Rel, RelB, p105-p50/NF-κB1, p100-p52/NF-κB2) and controls the expression of hundreds of genes involved in cell cycle, differentiation, and apoptosis, as well as inflammation and immune responses. There are two known NF-κB activation pathways. The first pathway is termed classical or canonical, where NF-κB activation depends on phosphorylation by the IKB kinases (IKKs) and degradation of the inhibitor of NF-κB (IKB) proteins. In the absence of stimulation, ubiquitous NF-κB dimers usually lie latent in the cell cytosol, bound to IκB proteins (IκB-α, IκB-β, or IκB-ε). IκBs mask the nuclear localization signal (NLS) of NF-κB proteins, keeping them inactive.

After phosphorylation by IKKs and proteasome degradation of IκB proteins, activated NF-κB complexes migrate into the nuclei and activate transcription of coordinate sets of target genes, thus promoting a variety of effects (e.g., inflammation, cell growth, cell death, or cell survival) in a cell-dependent fashion. For example, while NF-κB activation in the intestinal epithelia acts to maintains cell integrity and homeostasis, its expression in smooth muscle cells leads to inflammation and apoptosis. Similar to muscle cells, studies done elsewhere suggest a direct relationship between the over-expression of NF-κB Signaling with inflammation and cell death in the auditory sensory epithelia.

The heterocyclic compound quinoxaline (a.k.a. benzopyrazine) and its derivatives are used in the production of dyes, in pharmaceutical compounds and antibiotics. Quinoxaline has potential anti-tumoral properties and is known to block NF-κB signaling by inhibiting IKKκ and blocking NF-κB nuclear translocation, thereby inhibiting inflammation and apoptosis, as illustrated in FIG. 1.

The present disclosure relates to methods of treating acquired sensorineural hearing loss and/or ototoxicity in mammals by administering quinoxaline or a pharmaceutically acceptable derivative thereof. In implementations, quinoxaline and its derivatives can have a protective effect on hair cells on hair cells by blocking NF-κB signaling and nuclear translocation. Quinoxaline and its derivatives can also have a therapeutic effect of stimulating proliferation of existing sensory cells to restore lost hearing. In some implementations, quinoxaline can be administered as a pre-treatment prior to, or in conjunction with, exposure to ototoxic pharmaceutical agent(s) and/or acoustic trauma to prevent or decrease cochlear hair cell cytotoxicity and/or stimulate cochlear hair cell proliferation. In other implementations, quinoxaline can be administered as a treatment following exposure to ototoxic pharmaceutical agent(s) and/or acoustic trauma to stimulate cochlear hair cell proliferation.

Quinoxaline, as used herein, includes to a heterocyclic compound containing a ring complex made up of a benzene ring and a pyrazine ring, and its pharmaceutically acceptable derivatives.

EXAMPLE IMPLEMENTATIONS

In implementations, quinoxaline can have a preventative and/or a therapeutic effect on hair cells exposed to ototoxins (e.g., antibiotics, platinum-based antineoplastic agents, salicylates, quinine, loopdiuretic drugs, etc.) or harmful noises. In an example implementation, the in vitro and in vivo effects of quinoxaline (Sigma-Aldrich, St. Louis, Mo.) on cisplatin-treated cell lines and inner ear sensory epithelia were tested. Cisplatin is a platinum-based antineoplastic agent with a known strong cytotoxic effect.

Example 1

In vitro chemoprotective and proliferative quinoxaline effects in human mesenchymal cell line and mouse-derived neural cell line.

In one implementation, a human mesenchymal cell line (HT 1080), and a mouse-derived neural cell line (N2a), were used to measure the in vitro dose kinetics for quinoxaline and cisplatin. Cytotoxicity effects for each drug were measured by the colorimetric MTT assay. The MTT assay includes a yellow tetrazole that is reduced to purple formazan in living cells. In this implementation, solubilization solution (e.g., dimethyl sulfoxide, an acidified ethanol solution, or a solution of the detergent sodium dodecyl sulfate in diluted hydrochloric acid) was added to dissolve the insoluble purple formazan product into a colored solution. The absorbance of this colored solution was quantified by measuring at a certain wavelength (e.g, between 500 and 600 nm) by a spectrophotometer where the degree of light absorption depends on the solvent. The MTT assay can provide a useful measure of cell viability and proliferation. To quantify cytotoxicity, 10 µl of 10 mg/ml of MTT reagent was added to a well containing cells, and the cells were incubated at 37° C. for 4 hours. The supernatant was aspirated and the purple-colored formazan product was dissolved in 100 µl of DMSO. Absorbance was measured at 590 nm. The average of triplicate wells was taken for each concentration of the drug, and cell viability was calculated by substituting the corresponding mean absorbance values using the following equation:

$$\% \text{ Cytotoxicity} = \frac{\text{(Untreated cells)} - \text{(Treated cells)}}{\text{Untreated cells*}} \times 100$$

Figure 2:
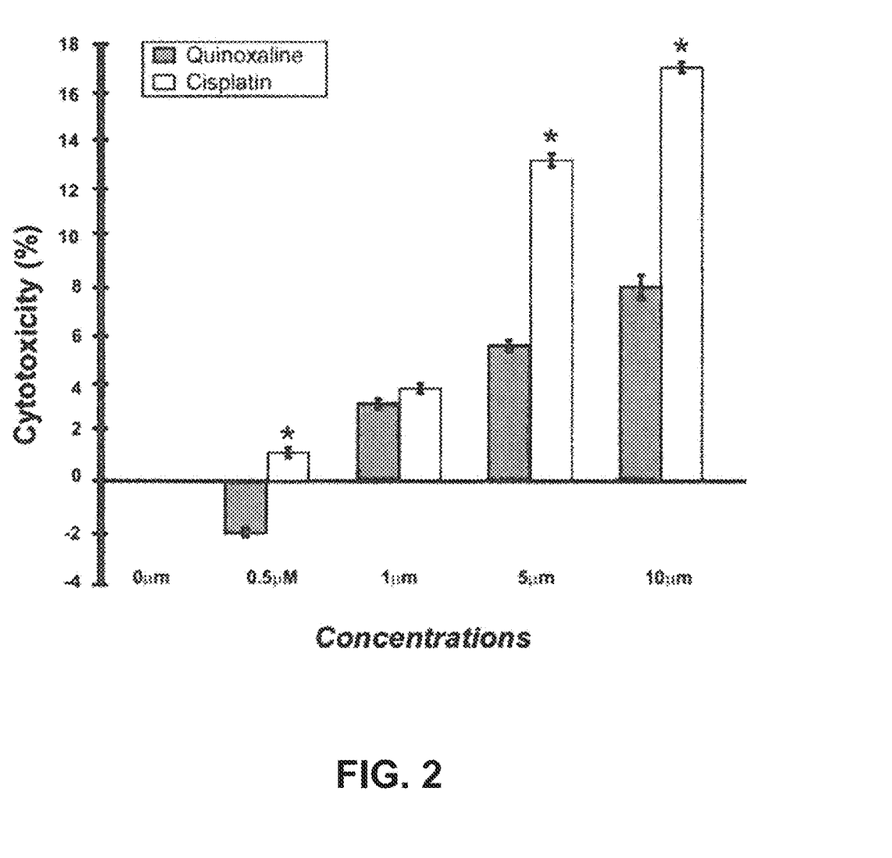
FIG. 2 is a diagram depicting in vitro dose kinetics for cisplatin and quinoxaline in accordance with an exemplary embodiment of the present disclosure.

FIG. 2 illustrates the cytotoxicity in HT 1080 cells at different doses of cisplatin and quinoxaline. A T-test (*=p<0.01; 0 μM=untreated cells) was used to compare toxicity between the two drugs at different concentrations. Cisplatin treatments resulted in cytotoxicity and cell death, particularly at concentrations higher than 1 μM. A direct relationship between cytotoxicity and increased quinoxaline doses was observed. Nevertheless, this cytotoxicity was consistently lower than that of cisplatin at all quinoxaline treatments. At the lowest concentration tested (0.5 μM), quinoxaline offered no toxicity and also had a modest, but quantifiable, positive effect on cell proliferation as shown by an increase in the total number of cells in samples. No statistically significant differences were observed between HT 1080 and N2a cell responses to cisplatin and quinoxaline treatments, as illustrated in FIG. 2. However, at concentrations greater than 25 μM, N2a cells were on average 30% more sensitive to cisplatin (higher cytotoxicity) than HT 1080 cells, as illustrated in FIGS. 2 and 3A.

Figure 3A:
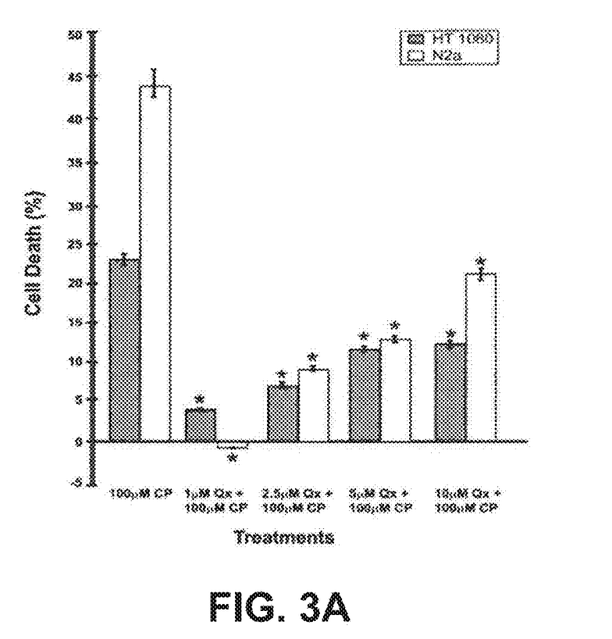
FIG. 3A is a diagram depicting in vitro chemoprotective and proliferative effects of quinoxaline (QX) on HT 1080 (mesenchymal) and N2a (neural crest) cells in accordance with exemplary embodiments of the present disclosure.

FIG. 3A illustrates the in vitro protective potential of quinoxaline pre-treatments on cisplatin-treated N2a and HT 1080 cells. Cells were plated at a density of 20,000 cells per well overnight, followed by a pretreatment with varying concentrations of quinoxaline for one hour. Thereafter, cells were treated with 100 μM cisplatin and incubated for 24 hours. Experiments were repeated three times for each cell line. Contrasting with the positive control group (100 μM cisplatin only), combined quinoxaline-cisplatin treatments significantly reduced overall cytotoxicity, hence protecting cells from cisplatin effects. N2a cells were significantly more sensitive to cisplatin than HT 1080. Moreover, at its lower concentration (see N2a bar for 1 μM quinoxaline concentration), quinoxaline not only protected neural crest-derived cells, but it also promoted their proliferation.

Example 2

In vitro quinoxaline chemoprotective and proliferative effects in inner ear-specific cells.

In an implementation, HEI-OC1 cells were treated with different concentrations (e.g., 200 nM, 500 nM, 1 μM, and 5 μM) of quinoxaline for 24-hours. Untreated cells were used as control groups. To quantify potential changes in cell proliferation following the treatment, DNA isolated from treated and untreated cells was submitted to CYQUANT analysis (Invitrogen, Grand Island, N.Y.), following the manufacturer's instructions for cell proliferation assay. The CYQUANT assay is based on the principle that cell number is proportional to the measurement of cellular DNA content. However, the use of the CYQUANT assay is offered by way of example only and is not meant to be restrictive of the present disclosure. In other embodiments, other types of cell proliferation assays can be used to quantify potential changes in cell proliferation.

Figure 3B:
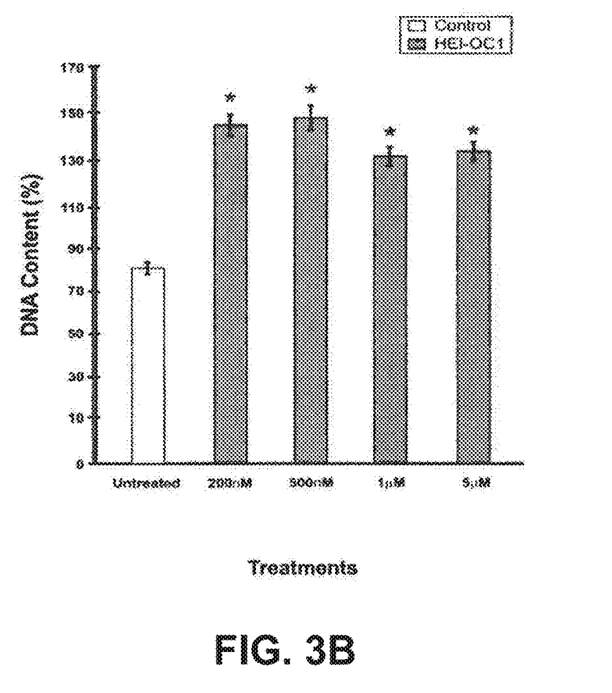
FIG. 3B is a diagram depicting in vitro chemoprotective and proliferative effects of quinoxaline (QX) on inner-ear specific HEI-OC1 cells in accordance with exemplary embodiments of the present disclosure.

FIG. 3B illustrates the DNA content of untreated cells and quinoxaline-treated cells. Consistent with the results described above for N2a and HT 1080 cells, as well as with quinoxaline's positive effect in cell proliferation, a statistically significant increase in DNA content (t-test, $p<0.001$) was observed in all quinoxaline-treated cells. Quinoxaline's effect in cell proliferation was most noticeable when cells were treated with lower concentrations (i.e., 200 nm and 500 nM) of the drug. Thus, lower quinoxaline concentrations also proved to be more efficient in protecting HEI-OC1 cells from cisplatin-induced death.

Figure 3C:
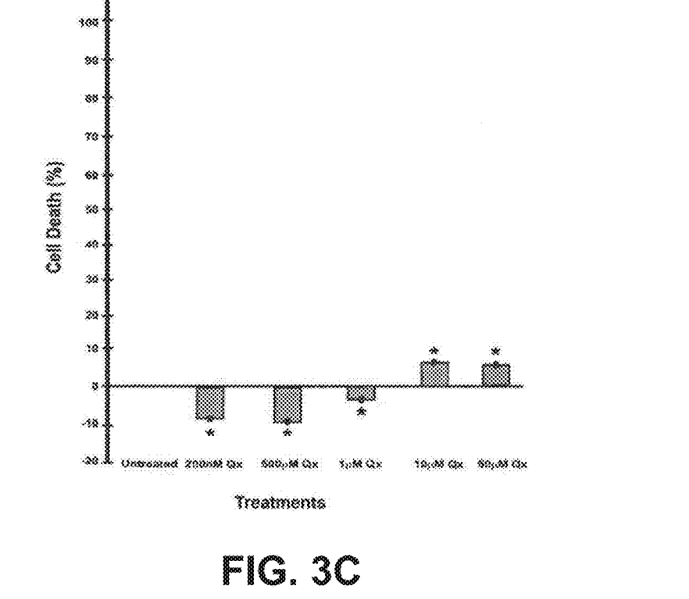
FIG. 3C is a diagram depicting in vitro cytotoxicity of quinoxaline (QX) in inner-ear specific HEI-OC1 cells in accordance with exemplary embodiments of the present disclosure.

As previously done for HT 1080 and N2a cells, the potential cytotoxicity of quinoxaline was measured in HEI-OC1 cells. HEI-OC1 cells were treated with a crescent dosage of quinoxaline (i.e., 200 nM, 500 nM, 1 μM, 10 μM, 50 μM) for 24 hours and submitted to MIT analyses. Similar to our earlier observations (illustrated in FIGS. 2 and 3A), an increase in cell proliferation was observed for cells treated with lower doses of quinoxaline, as illustrated in FIG. 3B. However, HEI-OC1 cells were particularly sensitive to quinoxaline concentrations higher than 5 μM, as illustrated in FIGS. 3B and 3C. Lower quinoxaline doses proved to be safer for HEI-OC1 cells, as dosages higher than 10 μM resulted in smaller, but quantifiable cell death, as illustrated in FIG. 3C. However, no statistically significant differences were observed in HEI-OC1 cytotoxicity at concentrations higher than 10 μM (FIGS. 3B and 3C).

Figure 3D:
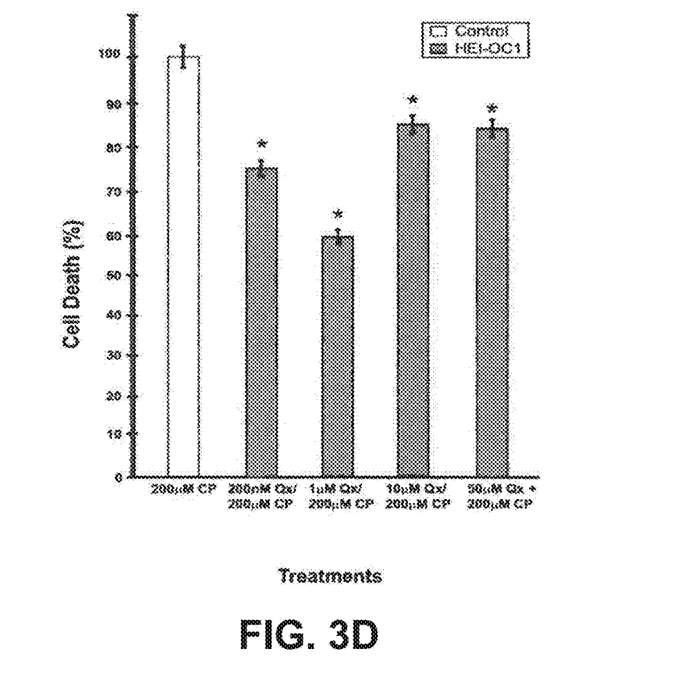
FIG. 3D is a diagram depicting in vitro cytotoxicity of quinoxaline (QX) on cisplatin-treated inner-ear specific HEI-OC1 cells in accordance with exemplary embodiments of the present disclosure.

FIG. 3D illustrates cytotoxicity the in vitro protective potential of quinoxaline pre-treatments on cisplatin-treated HEI-OC1 cells. HEI-OC1 cells were plated at a density of 20,000 cells per well overnight, followed by a pre-treatment with varying concentrations of quinoxaline (i.e., 200 nM, 1 μM, 10 μM, and 50 μM) for one hour. Thereafter, cells were treated with 200 μM cisplatin for 24 hours, Control samples consisted of HEI-OC1 cells treated with cisplatin only. 100% cytotoxicity was observed in the control samples, as illustrated in FIG. 3D. In contrast, a 25% (200 nM quinoxaline+200 μM cisplatin) to 40% (1 μM quinoxaline+200 μM cisplatin) survival rate was observed for cells pre-treated with quinoxaline (FIG. 3D). No statistically significant differences in cell survival were observed for HEI-OC1 cells pre-treated with higher than 10 μM quinoxaline.

Example 3

In vivo quinoxaline chemoprotective and proliferative effects on cochlear hair cells.

In an implementation, adult (24 days old) C57BL/6 and FVB mice were treated with cisplatin (20 mg/Kg of body weight) alone or combined with quinoxaline (15 mg/mL and 25 mg/mL) pre-treatment. The inner ear neurosensory epithelia, the organ of Corti (OC), were analyzed.

Figure 4A:
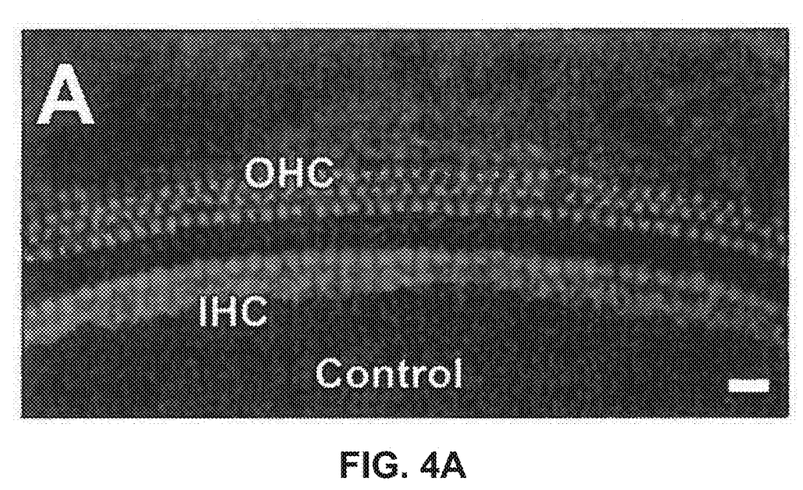
FIGS. 4A-4D are microscopy depictions of in vivo chemoprotective and proliferative effects of quinoxaline (QX) as evidenced by the presence of outer hair cells (OHC) and inner hair cells (IHC) in the auditory sensory epithelia in accordance with exemplary embodiments of the present disclosure.
Figure 4B:
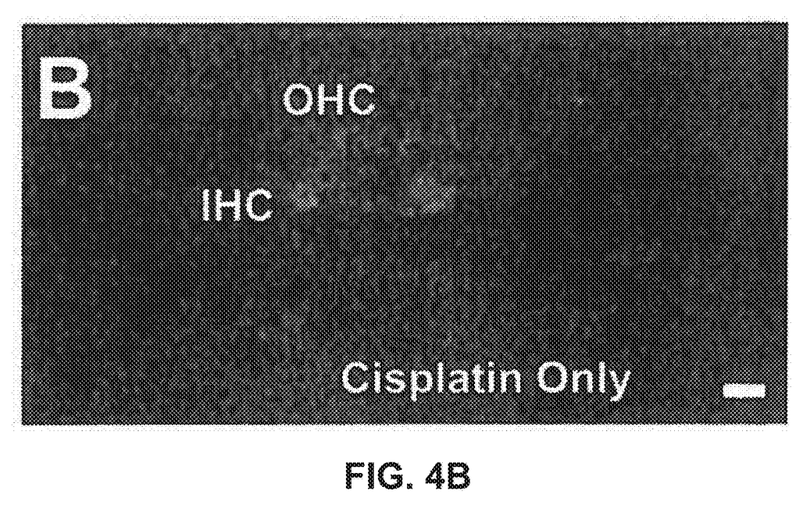
Figure 4C:
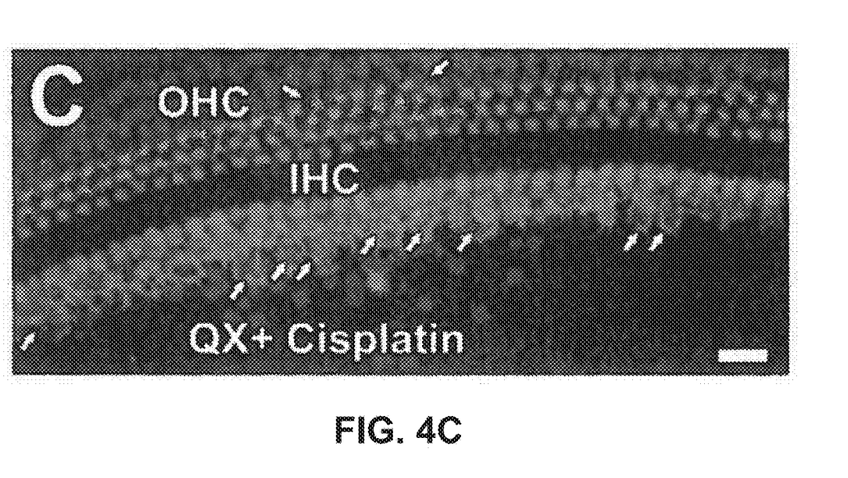
Figure 4D:
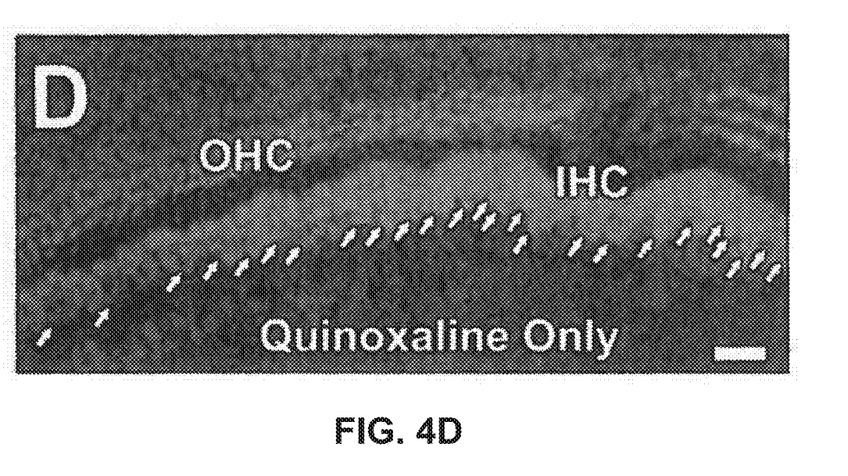

FIGS. 4A through 4D illustrate the outer hair cells (OHCs) and inner hair cells (IHCs) in the middle turn of the cochlea of adult C57BL/6 mice submitted to different treatments. The control group was the untreated cochlea, illustrated in FIG. 4A. Contrasting with the ears of animals treated with cisplatin only (FIG. 4B), myosin VIIa-positive hair cells were still observed on quinoxaline pre-treated ears, as illustrated in FIG. 4C. Additionally, supernumerary myosin VIIa-positive cells were observed at the IHC (indicated by white arrows) region). At low doses (e.g., 15 mg) quinoxaline can also affect cell proliferation, as demonstrated by an increase in the numbers of supernumerary cells (indicated by white arrows), as illustrated in FIG. 4D.

Example 4

Quinoxaline as preventative and/or therapeutic treatment for acquired sensorineural hearing loss.

In some embodiments, quinoxaline can be administered as a pre-treatment and/or treatment for acquired sensorineural hearing loss linked to damage of cochlear hair cells. For example, quinoxaline can be administered to humans or other mammals to prevent and/or treat ototoxicity and hearing loss resulting from ototoxic pharmaceutical agents. In some implementations, quinoxaline can be administered in conjunction with an ototoxic pharmaceutical agent. In other implementations, humans or other mammals can be pre-treated with quinoxaline prior to exposure to the ototoxic pharmaceutical agents. In some implementations, quinoxaline can be administered alone to stimulate ear cell proliferation.

In other embodiments, quinoxaline can be administered as a pre-treatment and/or treatment to humans or other mammals to prevent and/or treat hearing loss caused by acoustic trauma (e.g., exposure to harmful noises). In some implementations, quinoxaline can be administered prior to anticipated exposure to a potentially traumatic stimuli (e.g., harmful noise of 85 dB or greater). In other embodiments, quinoxaline can be administered following exposure to a potentially traumatic stimuli (e.g., harmful noise of 85 dB or greater) to stimulate cochlear hair cell proliferation.

The use of the quinoxaline as a pre-treatment and/or treatment for exposure to ototoxic pharmaceutical agents or acoustic trauma is offered by way of example only and is not meant to be restrictive of the present disclosure. In other embodiments, quinoxaline can be used as a pre-treatment or treatment for acquired sensorineural hearing loss due other causes linked to cochlear hair cell damage (e.g., disease or infection, aging, etc.).

In implementations, methods of administering quinoxaline alone or in combination with other active ingredients can include compositions suitable for oral, rectal, and parenteral administration (including subcutaneous, intrathecal, intramuscular, and intravenous). The most suitable route in any given case will depend on the nature and severity of the condition being-treated.

Solid pharmaceutical dosage forms comprising quinoxaline for use in conjunction with the present invention may be prepared by conventional compounding means. Such dosage forms can include, for example, those suitable for oral, rectal, nasal, topical (including buccal and sub-lingual) or vaginal administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may be presented as discrete units such as capsules, cachets or tablets each containing a predetermined amount of the active ingredient(s). Tablets and capsules for oral administration may contain conventional excipients such as binding agents, fillers, lubricants, disintegrants, or wetting agents. Solid dosage forms can include non-toxic solid carriers including, but not necessarily limited to, pharmaceutical grades of: mannitol, lactose, starch, magnesium stearate, sodium saccharin, the polyalkylene glycols, talcum, cellulose, glucose, sucrose magnesium carbonate, and so forth. Tablets may be coated according to methods well known in the art of pharmacy.

An exemplary solid dosage form in accordance with the present disclosure can comprise a tablet including quinoxaline, and lactose as a non-toxic solid carrier. The tablet can also include other active pharmaceutical ingredients (e.g., one or more ototoxic pharmaceutical agents). However, the use of the lactose as a non-toxic solid carrier is offered by way of example only and is not meant to be restrictive of the present disclosure. In other embodiments, a tablet can include other non-toxic solid carriers (e.g., mannitol, magnesium stearate, cellulose, etc.), or a combination thereof.

Pharmaceutical suspensions according to the invention can be formulated for oral administration and may contain conventional additives such as suspending agents, emulsifying agents, non-aqueous vehicles (which may include edible oils), or preservatives.

It is to be understood that embodiments of the present invention described above are intended to be merely exemplary. Those skilled in the art will recognize, or be able to ascertain using no more than routine experimentation, numerous equivalents to the specific procedures described herein. All such equivalents are considered to be within the scope of the present invention and are covered by the following claims.

It is further contemplated that any embodiment or implementation of the disclosure manifested above as a system or method may include at least a portion of any other embodiment or implementation described herein. Those having skill in the art will appreciate that there are various embodiments or implementations by which systems and methods described herein can be implemented, and that the implementation will vary with the context in which an embodiment of the disclosure is deployed.

Furthermore, it is to be understood that although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A method of treating ototoxicity in a mammal in need of such treatment, comprising:
   administering a therapeutically effective amount of quinoxaline to the mammal to proliferate cochlear hair cells.

2. The method of treating ototoxicity in a mammal of claim 1, wherein the quinoxaline is administered intravenously, transdermally, or orally.

3. The method of treating ototoxicity in a mammal of claim 1, wherein the therapeutically effective amount of the quinoxaline is from 15 mg/mL to 25 mg/mL.

4. The method of treating ototoxicity in a mammal of claim 1, wherein the quinoxaline is administered in solid form.

5. The method of treating ototoxicity in a mammal of claim 1, wherein the ototoxicity is caused by exposure to at least one of an ototoxic pharmaceutical agent or acoustic trauma.

6. The method of treating ototoxicity in a mammal of claim 5, wherein the ototoxic pharmaceutical agent is cisplatin.

7. The method of treating ototoxicity in a mammal of claim 1, wherein the quinoxaline is administered following exposure of the mammal to at least one of an ototoxic pharmaceutical agent or acoustic trauma.

8. A method of treating acquired sensorineural hearing loss in a mammal in need of such treatment, comprising:
   administering a therapeutically effective amount of quinoxaline to the mammal to proliferate cochlear hair cells.

9. The method of treating acquired sensorineural hearing loss in a mammal of claim 8, wherein the quinoxaline is administered intravenously, transdermally, or orally.

10. The method of treating acquired sensorineural hearing loss in a mammal of claim 8, wherein the therapeutically effective amount of the quinoxaline is from 15 mg/mL to 25 mg/mL.

11. The method of treating acquired sensorineural hearing loss in a mammal of claim 8, wherein quinoxaline is administered in solid form.

12. The method of treating acquired sensorineural hearing loss in a mammal of claim 8, wherein the hearing loss is caused by exposure to at least one of an ototoxic pharmaceutical agent or acoustic trauma.

13. The method of treating acquired sensorineural hearing loss in a mammal of claim 8, wherein the quinoxaline is administered following exposure of the mammal to at least one of an ototoxic pharmaceutical agent or acoustic trauma.

14. A method of treating ototoxicity in a mammal in need of such treatment, comprising:
   administering a therapeutically effective amount of quinoxaline to the mammal, wherein the therapeutically effective amount is from 15 mg/mL to 25 mg/mL;
   in combination with at least one ototoxic pharmaceutical agent to the mammal.

15. The method of treating ototoxicity in a mammal of claim 14, wherein the quinoxaline is administered intravenously, transdermally, or orally.

16. The method of treating ototoxicity in a mammal of claim 14, wherein the mammal is a human.

17. The method of treating ototoxicity in a mammal of claim 14, wherein the quinoxaline is administered prior to administration of the at least one ototoxic pharmaceutical agent to the mammal.

18. The method of treating ototoxicity in a mammal of claim 14, wherein the at least one ototoxic pharmaceutical agent is cisplatin.

19. The method of treating ototoxicity in a mammal of claim 14, wherein the quinoxaline is administered in solid form.

20. The method of treating ototoxicity in a mammal of claim 19, wherein the solid form is a capsule.

* * * * *